United States Patent [19]
Porée et al.

[11] Patent Number: 6,160,031
[45] Date of Patent: Dec. 12, 2000

[54] PROCESS FOR DECOMPOSING A POLYMER TO ITS MONOMER OR MONOMERS

[75] Inventors: Ian Douglas Porée; Karol Paula Cameron, both of Randburg; Janine Alison Bloem, Modderfontein; Fritz Dieter Schlosser, Johannesburg; Alison McGowan, Bryanston, all of South Africa

[73] Assignee: AECI Limited, Sandton, South Africa

[21] Appl. No.: 09/230,615

[22] PCT Filed: Jul. 25, 1997

[86] PCT No.: PCT/GB97/02032

§ 371 Date: May 19, 1999

§ 102(e) Date: May 19, 1999

[87] PCT Pub. No.: WO98/04599

PCT Pub. Date: Feb. 5, 1998

[30] Foreign Application Priority Data

Jul. 29, 1996 [ZA] South Africa .......................... 96/6423

[51] Int. Cl.$^7$ ................ C08J 3/28; C08J 11/04; C07C 5/00
[52] U.S. Cl. ................. 522/153; 522/150; 522/154; 522/155; 522/156; 522/157; 522/158; 522/159; 522/160; 522/161; 521/40; 521/40.5; 521/41; 521/43.5; 521/44.5; 521/46; 204/157.15; 204/157.3; 204/157.43; 204/157.47; 204/157.4
[58] Field of Search ..................... 522/150, 153, 522/154, 155, 156, 158, 159, 160; 521/40, 40.5, 41, 43.5, 44.5, 46; 204/157.6, 157.3, 157.15, 157.47, 157.48

[56] References Cited

U.S. PATENT DOCUMENTS

| | | | |
|---|---|---|---|
| 3,021,269 | 2/1962 | Miller et al. ............................ | 522/150 |
| 3,766,031 | 10/1973 | Dillon ...................................... | 522/156 |
| 4,009,324 | 2/1977 | Freedman et al. ....................... | 523/127 |
| 4,052,278 | 10/1977 | Brown et al. ........................... | 523/300 |
| 4,104,205 | 8/1978 | Novotny et al. ........................ | 526/339 |
| 4,282,076 | 8/1981 | Boyton ................................ | 204/159.2 |
| 4,456,675 | 6/1984 | Anderson, Jr. et al. ................ | 430/256 |
| 4,469,817 | 9/1984 | Hayashi et al. ........................... | 521/45 |
| 4,665,101 | 5/1987 | Ficker . | |
| 4,762,484 | 8/1988 | Ficker . | |
| 5,055,167 | 10/1991 | Dummersdorf et al. . | |
| 5,362,759 | 11/1994 | Hunt et al. ........................... | 521/44.5 |
| 5,507,927 | 4/1996 | Emery ................. | 204/157.43 |
| 5,814,673 | 9/1998 | Khait ......................... | 521/40 |

FOREIGN PATENT DOCUMENTS

| | | |
|---|---|---|
| 0 063 654 | 11/1982 | European Pat. Off. . |
| 0 154 333 A2 | 9/1985 | European Pat. Off. . |
| 0 282 827 A2 | 9/1988 | European Pat. Off. . |

OTHER PUBLICATIONS

Klun et al. Rapid induced microwave depolymerization of Polyamide–6 Polymer (41) 2000 p. 4361–4365.

*Primary Examiner*—James J. Seidleck
*Assistant Examiner*—Sanza L McClendon
*Attorney, Agent, or Firm*—Marshall & Melhorn

[57] ABSTRACT

A process for decomposing a polymer which is capable of undergoing thermal depolymerization to its monomer or monomers, such as for example poly(methylmethacrylate), and for the recovery of at least one of the monomers, includes the steps of subjecting the polymer in solid, gel, partially molten or molten form to microwave heating for a time and at a temperature sufficient to decompose the polymer to produce the monomer or monomers in gaseous, liquid or solid form, without substantial decomposition of the monomer or monomers, and recovering at least one of the monomer or monomers. The monomer or monomers may then be reused for plymerisation.

12 Claims, 5 Drawing Sheets

PROCESS FOR DECOMPOSING A POLYMER TO ITS MONOMER OR MONOMERS

BACKGROUND OF THE INVENTION

This invention relates to a process for decomposing a polymer which is capable of undergoing thermal depolymerization to its monomer or monomers, and for recovery of at least one of the monomers, which monomer may be recycled to a polymerization process.

The conventional decomposition or depolymerization process for the depolymerization of waste poly(methyl metharcylate) ("PMMA") makes use of a lead bath reactor. The waste PMMA is crushed into chips (1 to 5 cm in diameter) and decomposed on the surface of the molten lead bath. The molten lead is maintained at 520 to 550° C. by means of a diesel burner which operates at about 900° C. In the reactor, depolymerization takes place producing a gaseous product which is (methyl methacrylate) monomer ("MMA"), which is condensed in a condenser, with a solid dross or ash remaining on the surface of the lead bath. The dross is composed mainly of carbonaceous material, lead (40–60% m/m Pb) and inorganic residues from pigments and additives. The crude monomer (approximately 85% MMA) may then be purified as follows. The monomer is washed in a 9% caustic solution (containing 40 ppm copper sulphate heptahydrate $CuSO_4.7H_2O$) which removes any traces of lead. The washings (containing approximately 12 ppm lead) are treated and discharged to a slimes dam, but represent a potential environmental hazard. The final purification step is a vacuum distillation at 65° C., to remove heavy organic impurities. This type of depolymerization reactor may be operated to produce refined monomer with an average purity of 99.3% and yield of 85%.

This type of depolymerization reactor has numerous disadvantages. The most significant disadvantage of the lead bath reactor is the environmental and safety hazard associated with lead. Another disadvantage of the reactor is that it has to be operated on a non-continuous basis. Generally, the reactor is shut down after approximately five days operation due to fouling on the surface caused by the dross, which inhibits heat transfer from the lead to the PMMA. The cooling and cleaning operation may result in one co two days downtime. A further disadvantage is that the lead containing dross is generated as a waste product. Lead must be recovered from the dross, which then needs to be disposed of in an environmentally suitable manner. The lead bath subsequently must be reheated to operating temperature. Thus, this process is very energy inefficient.

In an article entitled Polymethyl Methacrylate Binder Removal from an Alumina Compact:Microwave versus Conventional Heating in Mat. Res. Soc. Symp. Proc. vol. 269, 1992 by moore et al, there is disclosed that compact samples of alumina and polymethyl methacrylate were heated in a 2450 MHz microwave cavity and by conventional heating in an electric furnace. Various heating schedules were used to effect the removal of the polymeric binder by thermal decomposition. Dielectric properties, porosity and other physical properties were investigated in order to better understand the binder removal process in a microwave field. Results of the study emphasized the amount of the carbon residuals remaining in the bulk. In this article it is stated that PMMA decomposes into monomer, water. benzene and other components. These components are then further decomposed to hydrocarbons between 500° C. and 1000° C. In other words, the PMMA is completely decomposed into hydrocarbons.

In an article entitled Microwave reactions of polyethylene terephthalate, in Polym.Mater.Sci.Eng, 71,531–2, 1994, by Gilmer et al, there is disclosed that a glass reactor was designed for the microwave cavity to allow conventional chemical reactions to be carried out with focused microwave heating. Employing this setup for reactions concerning the synthesis and depolymerization of poly(ethylene terephthalate) (PET), in general, the monomers for PET are not good microwave heaters (absorbers), with the possible exception of ethylene glycol (EG). In the depolymerization of PET by EG and the reaction of EG with di-methyl terephthalate to form bis (hydroxyethyl) terephthalate and methanol (MeOH), identical reaction rates were obtained using either thermal or microwave heating.

In other words, this article discloses in general the depolymerization of PET, in a solvent, i.e EG.

There is thus a need for a new process for decomposing a polymer to its monomer or monomers, which process makes use of an economic, safe and environmentally friendly thermal decomposition route which eliminates the use of lead, and which results in a lesser amount of "ash" or "dross" which is free of contamination by lead.

SUMMARY OF THE INVENTION

According to a first aspect of the invention there is provided a process for decomposing a polymer which is capable of undergoing thermal depolymerization to its monomer or monomers, the polymer being selected from the group consisting of poly(methyl methacrylate), polyterrafluoroethylene, polystyrene, poly(ethylene cerephthalate), poly(α-methylstyrene) and polyisobutylene, and for recovery of at least one of the monomers, which includes the steps of:

(i) subjecting the polymer in solid, gel, partially molten or molten form to microwave heating for a time and at a temperature sufficient to decompose the polymer to produce the monomer or monomers in gaseous, liquid or solid form, without substantial decomposition of the monomer or monomers; and (ii) recovering at least one of the monomer or monomers.

The polymer may be any suitable polymeric material which is capable of undergoing thermal depolymerization to its corresponding monomer or monomers, in reasonable yields, and which is selected from the list given above.

The polymer to be decomposed may be present as a single polymer, or in a mixture of two or more polymers. In this latter case, both or all the polymers may be as listed above, or one polymer may be as listed above, and the other polymer or polymers may be different polymers which may or may not decompose to their monomer or monomers.

The process of the invention is of particular application to poly(methyl methacrylate) which undergoes thermal depolymerization to methyl methacrylate, in up to 99% monomer yield.

The process of the invention may include the following steps:

(iii) where two or more monomers are recovered in step (ii), separating the monomers from one another;

(iv) where the monomer or monomers are in gaseous form, condensing the monomer or monomers; and (v) purifying the condensed monomer or monomers.

Thereafter, the monomer or monomers may, for example, be recycled to a process for polymerization of the monomer or monomers to produce the polymer, or other polymers, or may be used to manufacture other products.

Prior to step (i), the polymer may be preheated to a suitable temperature. The heating may be carried out in any conventional manner.

In step (i), the polymer may be mixed with a microwave absorber or susceptor, i.e. a material with a high dielectric loss factor. Examples of suitable microwave absorbers or susceptors are carbon powder (carbon black, furnace black, lampblack); FREQUON B20 which is a fine white inorganic powder; $M(O_3ZO_xR)_n$ where M=metal, Z=group V atoms with molecular weight $\geq 30$, x=0.1, R=H or organic radical. n=1.2, for example $Zr(O_3PCH_2CH_2SH)$; high loss ceramics, such as silicon carbide (SiC); ferrites; most electro-ceramics (e.g. barium titanate, $BaTiO_3$); and alkali metal oxide-based materials (e.g. sodium oxide). The use of a microwave absorber or susceptor may enhance the decomposition process, in polymers which themselves do not interact or interact only poorly with microwaves (such as non-polar materials.).

Step (i) may be carried out under an inert atmosphere, for example a nitrogen atmosphere.

In step (i), the microwave heating may be carried out in a mono-mode, a multi-mode or a non-resonant cavity of a microwave reactor, at any suitable microwave frequency, and preferably at 2.45 GHz or 915 MHz, which are industrial frequencies.

The process of the invention may be carried out on a continuous or on a batch basis.

According to a second aspect of the invention there is provided the use of a monomer produced by the process described above in a process for the polymerization of the monomer, optionally with one or more additional monomers, and optionally mixed with virgin monomer in a suitable ratio, to produce a polymer, and also to the process of polymerization.

DESCRIPTION OF EMBODIMENTS

Figure 1:
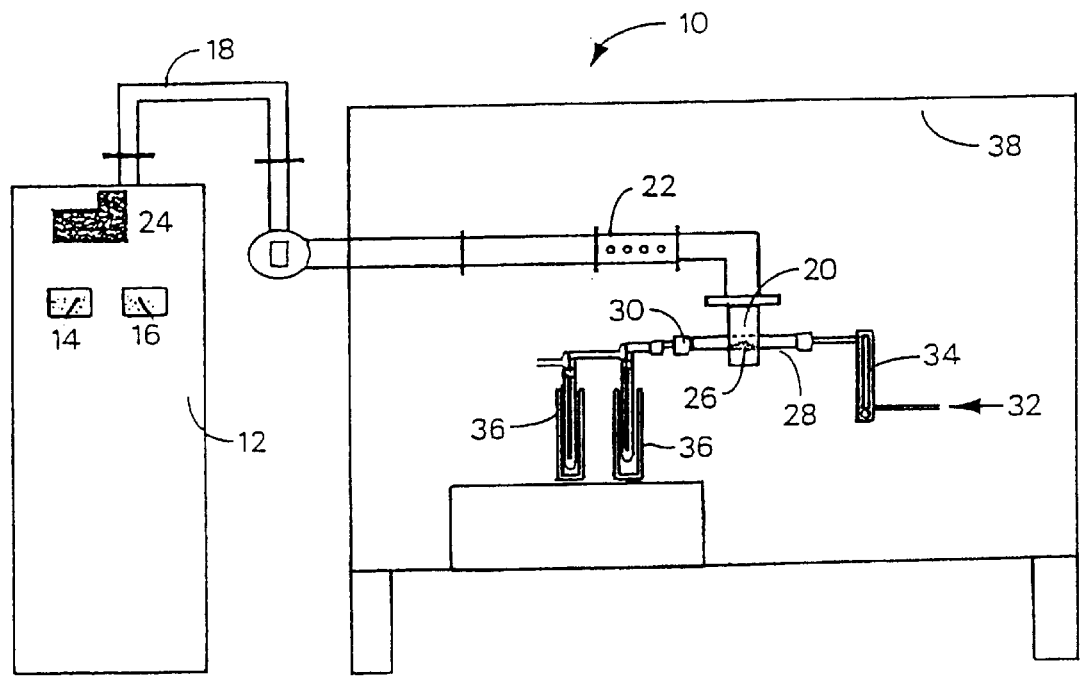
FIG. 1 is a diagrammatic cross-sectional view of a laboratory scale mono-mode microwave apparatus for use in the process of the invention.

The crux of the invention is a process for decomposing a polymer which is capable of undergoing thermal depolymerization to its monomer or monomers, the polymer being selected from the group consisting of poly(methyl methacrylate), polytetrafluoroethylene, polystyrene, poly (ethylene terephthalate), poly($\alpha$-methylstyrene) and polyisobutylene, and for recovery of at least one of the monomers, which includes the steps of:

(i) subjecting the polymer in solid, gel, partially molten or molten form to microwave heating for a time and at a temperature sufficient to decompose the polymer to produce the monomer or monomers in gaseous, liquid or solid form, without substantial decomposition of the monomer or monomers; and (ii) recovering at least one of the monomer or monomers.

As the purpose of the invention is to recover at least one of the monomers the microwave heating must be such that the monomer to be recovered is not substantially decomposed further. Thus, the phrase "without substantial decomposition of the monomer or monomers" must be interpreted in this way.

It is to be noted that the polymer is subjected to the microwaves in solid, gel, partially molten or molten form. In other words, step (i) is carried out in the absence of a solvent or solvents for the polymer.

By a "gel" there is meant a system which contains a range of products from monomer through to the polymer, i.e a partially polymerized mixture. The system contains no solvent for the polymer.

The process of the invention is of particular application to polymers selected from the group consisting of poly(methyl methacrylate), polytetrafluoroechylene, polystyrene, poly ($\alpha$-methylstyrene) and polyisobutylene, i.e excluding poly (ethylene terephthalate), since degradation of this polymer to recover both monomers, ethylene glycol and terephthalic acid, involves an hydrolysis reaction, which requires the presence of a suitable solvent such as ethylene glycol or another hydroxy containing species, for example methanol. In the process of this invention, only terephthalic acid may be recovered in the absence of a solvent.

The process of the invention is more especially of application to poly(methyl methacrylate).

As stated above, the polymer to be decomposed may be present as a single polymer or in a mixture of two or more polymers. In this latter case, both or all the polymers may be as listed above, or one polymer may be as listed above, and the other polymer or polymers may be different polymers which may or may not decompose to their monomer or monomers.

Thus the process may be used selectively to decompose and recover the monomer of one polymeric substance, or to decompose and recover two or more monomers consecutively, from a co-polymer or physical mixture of several polymers, where the decomposition temperatures and the dielectric loss factors are suitably different to allow this. In the process, the temperature of decomposition is controlled so as to prevent substantial further degradation of the monomer or monomers to undesirable hydrocarbons or other carbonaceous materials.

As stated, the process of the invention is of particular application for the depolymerization of acrylic resins and polymers, more particularly poly(methyl methacrylate), or co-polymers and physical mixtures of poly(methyl methacrylate) with other polymeric substances.

The polymer may be treated in gel, partially molten or molten form, or in solid form in the form of chips, for example having a diameter of from 0.1 to 5 cm, or in the form of a powder.

The process is of particular application for the depolymerization of both cast and extruded acrylic products and high impact acrylic products which may contain other recyclable (e.g. polystyrene) or non-recyclable components.

It is also of use in the recycling of powdered waste PMMA and acrylic products, also known as swarf, which arises from the cutting of PMMA and acrylic products, and PMMA gel (partially polymerized PMMA/MMA mixture).

In step (i) the polymer may be mixed with a microwave absorber or susceptor, i.e. a material with a high dielectric loss factor. An example of a suitable microwave absorber or susceptor is carbon black. Other examples are given above. Carbon black is a very efficient microwave absorber and heats up within seconds, enhancing the decomposition of the polymer. The thermal energy is transferred from the carbon black to the polymer resulting in rapid decomposition. The percentage by mass of the carbon black added may be from 0.5 to 50%, preferably from 0.5 to 5% by mass of the polymer. The carbon black is unaffected in the inert atmosphere and can therefore be recycled, provided that residual inorganic pigments do not interfere with the process.

It is not, however, always necessary to use a microwave absorber or susceptor. By optimization of the cavity design (geometry and dimensions), coupling with the material to be heated is maximized, reducing the need for a susceptor. For example, in the case of PMMA, after optimization of the reactor design, no microwave absorber or susceptor was required, since PMMA coupled efficiently with the microwave energy.

Step (i) may be carried out under an inert atmosphere, e.g. a nitrogen atmosphere. The nitrogen atmosphere is used to sweep the gaseous product out of the reaction zone and to prevent ignition of hot volatile organic vapors, in the case where the monomer is released as a flammable organic liquid or vapors. The nitrogen also serves to prevent ignition of carbon where this is used as a microwave susceptor.

Further, in order co prevent the condensation of the gaseous products on the walls of the microwave reactor, it is possible to heat the walls of the microwave reactor by conventional means.

Prior to step (i), the polymer may be preheated to a suitable temperature, the heating being carried out in any conventional manner.

The reason for this is that it has been found that the microwave absorption efficiency of some polymers, such as PMMA, increases with increased temperature. This property can be utillized to improve the overall efficiency of the process of the invention. Thus, the polymer may be preheated conventionally so as to improve the microwave absorption efficiency and then at the elevated temperature, the polymer is irradiated with microwave energy. The advantages of the preheating include the fact that the microwave absorption efficiency may be improved through more effective coupling of the energy with the polymer at the raised temperature and, the overall energy cost of the process may be reduced by hybrid heating, as the microwave heating is only used in the most effective decomposition (temperature) zone.

When the polymer is PMMA, the PMMA may be preheated to a temperature of from 80° C. to 150° C. inclusive. However, with appropriate design of the microwave apparatus, PMMA couples very effectively with the microwave energy, and pre-heating is nor necessary.

The microwave heating may be carried out in a monomode, a multi-mode or a non-resonant cavity of a microwave apparatus at any suitable microwave frequency as determined by dielectric property measurements and more preferably at an industrial frequency such as 2.45 GHz or 915 MHz. The microwave irradiation directly interacts with and heats the polymer, causing the decomposition to take place.

The microwave energy may be generated by a magnetron or klystron using electrical power. The microwaves are generated in a microwave generator and transferred into a mono-mode, or a multi-mode or a non-resonant cavity by means of a waveguide. Power requirements will depend on the dielectric properties of the material under irradiation at a particular frequency, the mass of material, the feed rate and the system efficiency.

The microwave apparatus preferably should allow for fine tuning of the microwave irradiation applied to the cavity to maximize the electric field density in the region of the polymer, and hence to improve the efficiency of depolymerization of the polymer.

The process may be carried out on a batch basis, or on a continuous basis by continuously feeding the polymer into the microwave cavity and, in the case of a gaseous product, sweeping the gaseous product out of the reaction zone. The inert sweep gas may pass either co-currently or countercurrently co the passage of the polymer. The process also may be operated without a continuous inert gas sweep by suitable design of the equipment.

The residence time of the polymer under microwave irradiation will be determined so as to obtain the desired decree of decomposition of the polymer, without substantial decomposition of the monomer occurring, and is also related to the type and mass of the polymer being decomposed the dielectric properties of the polymer, the feed rate, the power used, and the efficiency of the system design. As stated above preheating the polymer conventionally before microwave irradiation reduces the irradiation time required as the microwave absorption efficiency is improved.

Similarly, the use of a susceptor reduces the required irradiation time, which is again dependent on the above factors in addition to the ratio (m/m) of polymer to susceptor.

In general, it is desirable to limit the maximum temperature within the microwave apparatus so as to decompose the polymer to its monomer/monomers, without substantial further degradation of the monomer/monomers.

In the case of two polymers (i.e a mixture or co-polymer), in the absence of a susceptor, the upper temperature is largely determined by the polymer (I) with the highest dielectric loss factor, i.e that which absorbs or interacts most strongly with the microwave energy at a particular frequency. An example of this is the case of a mixture of PMMA and polystyrene, where the upper temperature is determined by the PMMA, due to its greater interaction with microwave energy. In this case, the maximum decomposition temperature is higher than the typical temperature range for decomposition of the second polymer (polystyrene). Provided that this temperature maximum does not exceed the temperature at which further degradation of the monomer from decomposition of the second polymer (II) occurs, both monomers from polymers (I) and (II) may be recovered, simultaneously. However, if the maximum temperature does exceed the degradation temperature for the second monomer, only monomer from the first polymer (I) may be recovered. This applies similarly for mixtures containing more than two polymers.

In the case of two or more polymers (i.e a mixture or co-polymer), in the absence of a susceptor, where the upper or maximum temperature, defined by the polymer (I) with the highest dielectric loss factor, is sufficiently below the temperature for decomposition of the second polymer (II) (and subsequent polymers, III, IV, etc.), then it may be possible to selectively decompose the first polymer and recover the monomer from polymer (I) selectively, prior to decomposition of the second polymer (II) (and subsequent polymers, III, IV, etc.) and recovery of the monomer (monomers). Invariably, some decomposition of the second and subsequent polymers may occur concomitantly with that of the first, to varying degrees, if the temperature ranges of decomposition overlap with that of the first polymer. Where the second polymer (II) (and/or subsequent polymers, III, IV, etc) does (do) not interact or interacts (interact) only poorly with microwaves, it may be necessary to add a suitable susceptor material to the reactor after the decomposition of the polymers which interact strongly with microwaves, in order to increase the temperature for further decomposition of the remaining polymers.

Generally, with PMMA, decomposition begins at around 300° C. and is complete by about 400° C. Further heating above 400° C. results in undesirable charring caused by the further decomposition of monomer to undesirable carbonaceous products.

Thus, it is essential to control temperature in the case of PMMA carefully and to prevent substantial increase in temperature above 400° C. This is a further reason for periodic removal of inorganic pigment residues, which may increasingly absorb microwave energy on accumulation, leading to thermal runaway and substantial charring of the product and reduced monomer purity and recovery.

In the case of polystyrene, the temperature range of decomposition should be limited to about 230° to about 400° C.

In the case of poly(ethylene terephthalate), the temperature range of decomposition should be limited to about 300° C. to about 450° C.

In the case of polytetrafluoroethylene, the temperature range of decomposition should be limited to about 450° C. to about 550° C.

In the case of poly(α-methylstyrene) the temperature range of decomposition should be limited to about 200° C. to about 500° C.

In the case of polyisobutylene the temperature range of decomposition should be limited to about 300° C. to about 400° C.

However, the above temperature limits, given as an indication, are defined for individual polymers and the upper temperature limits for mixtures naturally will be dependent on the composition of the polymer mixture/co-polymer, the gas atmosphere and the pressure under which decomposition is conducted. In the presence of a susceptor, temperature control is vital to prevent thermal runaway and to avoid substantial degradation of the monomer/monomers.

The products of step (i) are firstly the monomer or monomers in gaseous form and secondly a small amount of residue, which mainly comprises inorganic pigments and ash (carbon). The residue may be removed from the microwave reactor periodically by suitable design of the equipment to prevent ingress of oxygen or air into the reaction zone, or leakage of microwave energy from the reactor.

In the case of poly(ethylene terephthalate), terephthalic acid is recovered as the solid monomeric form from the microwave cavity itself.

After step (ii) which comprises recovery of the gaseous monomer or monomers, the gaseous monomer or monomers may be subjected to one or more of the following steps.

Where two or more monomers are recovered in gaseous or liquid form, the monomers may be separated from one another, for example by distillation. In the case of distillation the gaseous monomers are first condensed.

Thereafter, the monomer or monomers may be condensed by conventional means.

If necessary, the condensed monomer or monomers may be purified by conventional means before being recycled to a polymerization process, or prior to use in the manufacture of other products.

In the case of poly(ethylene terephthalate), the solid terephthalic acid recovered may be purified by conventional means.

The invention also covers the use of a monomer produced by the process described above in a process for the polymerization of the monomer, optionally with one or more additional monomers, and optionally mixed with virgin monomer in a suitable ratio, to produce a polymer.

Similarly the invention covers the use of the monomer produced by the process described above in the manufacture of other products.

For example, in the case of PMMA, the recovered monomer MMA may be used in the manufacture of acrylic resins, plastics and fibers, impact modifiers and processing acids, emulsion polymers, mineral-based sheet polyesters, polymer concrete and speciality methacrylares such as butyl methacrylate, stearyl methacrylate, decyl methacrylace and 2-ethylhexyl methacrylate.

In the case of polystyrene, the recovered styrene monomer may be used in the manufacture of acrylonitrile-butadiene-styrene (ABS) resins, styrene-acrylonitrile (SAN) resins, styrene-bucadiene (S/B) copolymer latexes, unsaturated polyester resins, styrene-butadiene rubber (SBR) elastomers and latexes, styrenated phenols, styrene oxide and styrenated oils.

In the case of poly(ethylene terephthalate), the recovered and purified terephthalic acid may be used in the manufacture of polyester films and fibers, poly(ethylene terephthalate) solid state resin, terephthaloyl chloride, dioctyl terephthalate, liquid crystal polymers, amorphous nylons, thermoplastic resins and dimethyl tetrachloroterephthalate, and as a raw material in fine organic chemical synthesis.

Figure 2:
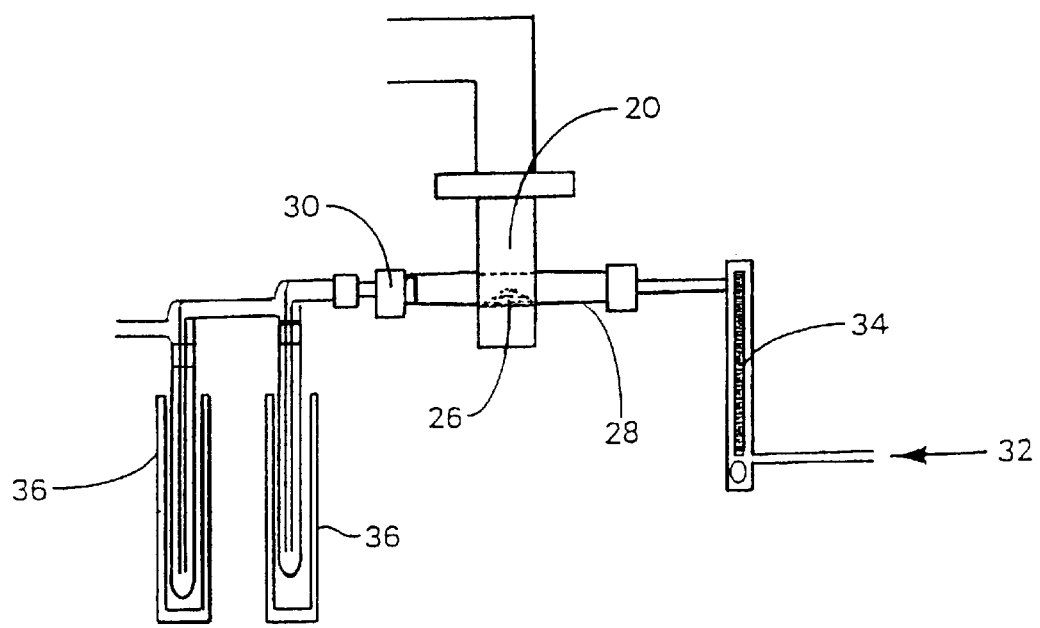
FIG. 2 is an expanded view of a portion of the mono-mode cavity of the apparatus of FIG. 1.

The invention will now further be described with reference to the accompanying drawings which are given by way of example only. Referring to FIGS. 1 and 2, there is shown a laboratory scale microwave apparatus 10. The apparatus 10 includes a 6 kW microwave variable power unit 12 with an operating frequency of 2.45 GHz. The power unit 12 is fitted with forward 14 and reflected 16 power gauges. To the power unit 12 there is attached a waveguide 18 with a mono-mode cavity 20 located in an opening in the waveguide 18 but designed to prevent any microwave leakage. The waveguide 18 is fitted with a stub tuner 22 to tune the microwave energy being supplied to the cavity 20 and an isolator 24 to absorb the reflected power. The microwave energy is transferred via the waveguide 18 to the mono-mode cavity 20 where it is absorbed by the polymer 26. A quartz tube 28 or other suitable microwave transparent vessel holds the polymer 26 inside the microwave cavity 20. The tube 28 is fitted with gas tight seals 30 to allow for efficient product recovery and an effective inert gas atmosphere. The inert gas is introduced at 32 and is controlled by a calibrated flow meter 34. The gaseous monomer product is condensed in two liquid nitrogen traps 36 or other suitable equipment. The apparatus 10 is located in a fume hood 38 for safety purposes to remove any organic vapours which are not condensed by the liquid nitrogen gas traps 36.

Figure 3:
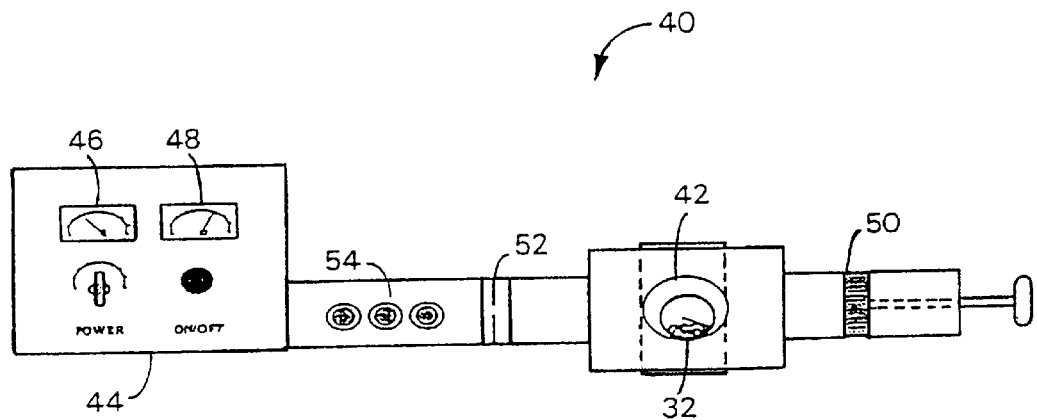
FIG. 3 is a diagrammatic cross-sectional view of a modification of the mono-mode cavity of the apparatus of FIG. 1.

Referring to FIG. 3, reference 40 generally indicates a modification of the mono-mode cavity 20 described in FIGS. 1 and 2, which includes additional features required to tune the microwave cavity to maximize the coupling of the microwave energy with the polymer being irradiated. The mono-mode cavity 40 comprises an opening in a waveguide 42 designed to prevent microwave leakage. The waveguide 42 is connected to a microwave variable power supply 44 which is fitted with reflected 46 and forward 48 power gauges. The waveguide 42 is fitted with an adjustable short circuit device 50, an adjustable iris 52 and graduated stub tuners 54, used to tune the microwave energy supplied to the cavity 40. By adjusting the position of the standing wave in the waveguide 42, it is possible to minimize the reflected power and maximize the coupling of the microwave energy with the polymer being irradiated.

Figure 4:
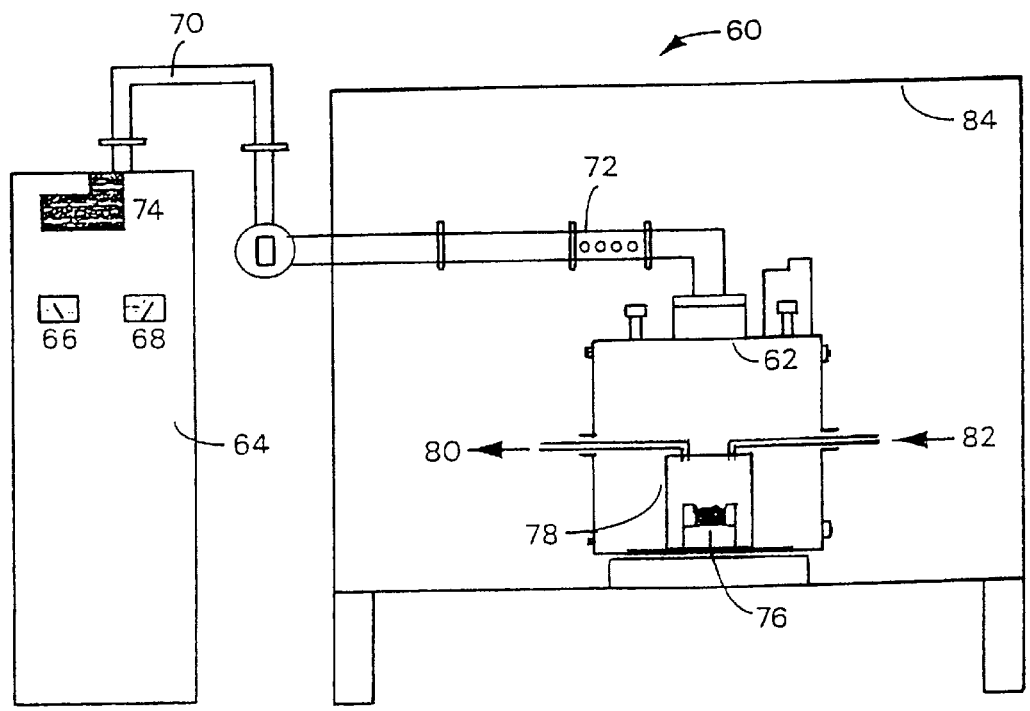
FIG. 4 is a diagrammatic cross-sectional view of a laboratory scale multi-mode microwave apparatus for use in the process of the invention.

Referring to FIG. 4 there is shown a laboratory scale microwave apparatus 60 fitted with a multi-mode cavity 62. The apparatus 60 includes a 6 kW microwave variable power unit 64 with an operating frequency of 2.45 GHz. The power unit 64 is fitted with reflected 66 and forward 68 power gauges. Attached to the power unit 64 is a waveguide 70. The multi-mode cavity 62 comprises a stainless steel cavity designed to contain the microwave energy supplied by the power unit 64. The waveguide 70 is fitted with a stub tuner 72 to tune the microwave energy being supplied to the cavity 62 and an isolator 74 to absorb the reflected power and thereby protect the magnetron. The microwave energy is transferred via the waveguide 70 to the cavity 62 where it is absorbed by a polymer 76. The polymer 76 may be placed directly in the cavity 62. Alternatively, the polymer is placed on a ceramic support inside a gas in-tight, microwave transparent container 78. Where the monomer is in gaseous form, the product is swept out of the microwave transparent container 78 and condensed outside the microwave cavity 62 through a gas outlet 80. The container 78 is constantly purged with an inert gas through a gas inlet 82. The whole apparatus is enclosed in a fume hood 84 for safety purposes.

Referring co FIG. 5(a), there is shown a bench scale (1.5–2 kilogram per hour semi-continuous) microwave apparatus 90 fitted with a mono-mode cavity 92. The apparatus 90 includes a 6 kW microwave variable power unit 94 (FIG. 5(b)) with an operating frequency of 2.45 GHz. (On an industrial scale a frequency of 915 MHz is more favourable.) The power unit 94 is fitted with forward 96 and reflected 98 power causes as shown in FIG. 5(b). Attached to the power unit 94 is a waveguide 100.

The mono-mode cavity 92 comprises a cylindrical stainless steel cavity 102. The mono-mode cavity 92 is specially designed so as to maximize the electric field in the lower section of the reactor 92 and the cavity is specially tuned by the creation of a small iris 104 in the center of the cavity wall where the waveguide 100 makes contact with the wall. The dimensions of the iris 104 are critical to maixmize energy coupling within the cavity 92. To prevent substantial quantities of the gaseous product from diffusing into and condensing in the waveguide 100, which could cause a fire, a quartz window (transparent to microwave energy) 106 is sealed in a flange 108, with a recess and special seals, in the section 110 of the waveguide 100 in contact with the reactor 92. This section 110 of waveguide 100 is jacketed to allow cooling (water or other suitable coolant). A nitrogen purge inlet 112 is located between this section 110 and the cavity wall 102 to prevent condensation of the gaseous product on the quartz window 106. As a precaution, in the event that the quartz window 106 should be damaged, a second quartz window/flange system 114 is located further up the waveguide 100, to protect the magnetron. The section of the waveguide between the quartz windows 106 and 114 is purged with nitrogen through an inlet 112. The nitrogen gas exists at outlet 116 and may be tested for the presence of monomer by a suitable gas sensing device (e.g a Dräger tube).

A polymer 118 is fed to the cavity 92 via a feed hopper 120. The feed hopper 120 is connected to a feed tube 122, sealed between two valves 124 and 126. A nitrogen inlet 128 allows this tube 122 to be pureed of oxygen during feeding. The operation involves opening the upper valve 124 while the lower valve 126 is closed, filling the tube 122 with polymer while purging with a nitrogen flow (inlet 128) and then closing the upper valve 124. The lower valve 126 is then opened to allow the polymer to fall through a section 130, heated with heating tape, before failing through a choke 132 purged with nitrogen through an inlet 134. The lower valve 126 is closed immediately thereafter, to prevent the diffusion of gaseous product into the feed mechanism, which may cause stickiness and result in blockage of the tube 122. The choke 132 is designed with suitable dimensions to prevent the leakage of microwave radiation from the cavity 92.

The polymer 118 falls through into the cavity 92, where it may be preheated (although this is not necessary in the case of some polymers, e.g PMMA) prior to irradiation with microwave energy by any conventional heating means, in this case a heating tape 136, set at a predetermined temperature. Where the monomer is recovered in gaseous form, the gaseous product arising from the decomposition of the polymer exits the reactor 92 through an outlet 138 (of suitable dimensions so as not to permit microwave leakage from the cavity) and passes along a heated line to a suitably designed and chilled condenser 140, prior to being collected in a suitable vessel 142 which may or may not be cooled further. Samples can be capped from the condensate collection vessel 142 at a sampling point 144, to allow the product purity and composition to be determined periodically during the reaction. Nitrogen puree gas exiting the system via the storage/collection vessel 142 at the exit point 146 is monitored continuously by an oxygen meter for safety purposes.

For safety, a pressure relief valve 148 and a pressure monitoring device 150 (e.g., manometer or pressure gauge) may be connected to the cavity 92 on an upper flange 152 on the cavity 92, provided that the dimensions are such that no leakage of microwaves occurs.

A thermocouple 154 is located in the gas outlet pipe 138 to monitor the temperature of the gaseous product prior to condensation. Another thermocouple 156 is located in the lower region of the cavity 92 (in the region of the polymer) to monitor the temperature during decomposition. The feed rate is controlled by monitoring the reflected power 98 (see FIG. 5(b)) and matching the feed rate to the decomposition rate in the cavity. The entire reactor 92 is insulated by encapsulating it in a suitable refractory (insulating) material such as Fibrefrax™ 158.

Figure 6:
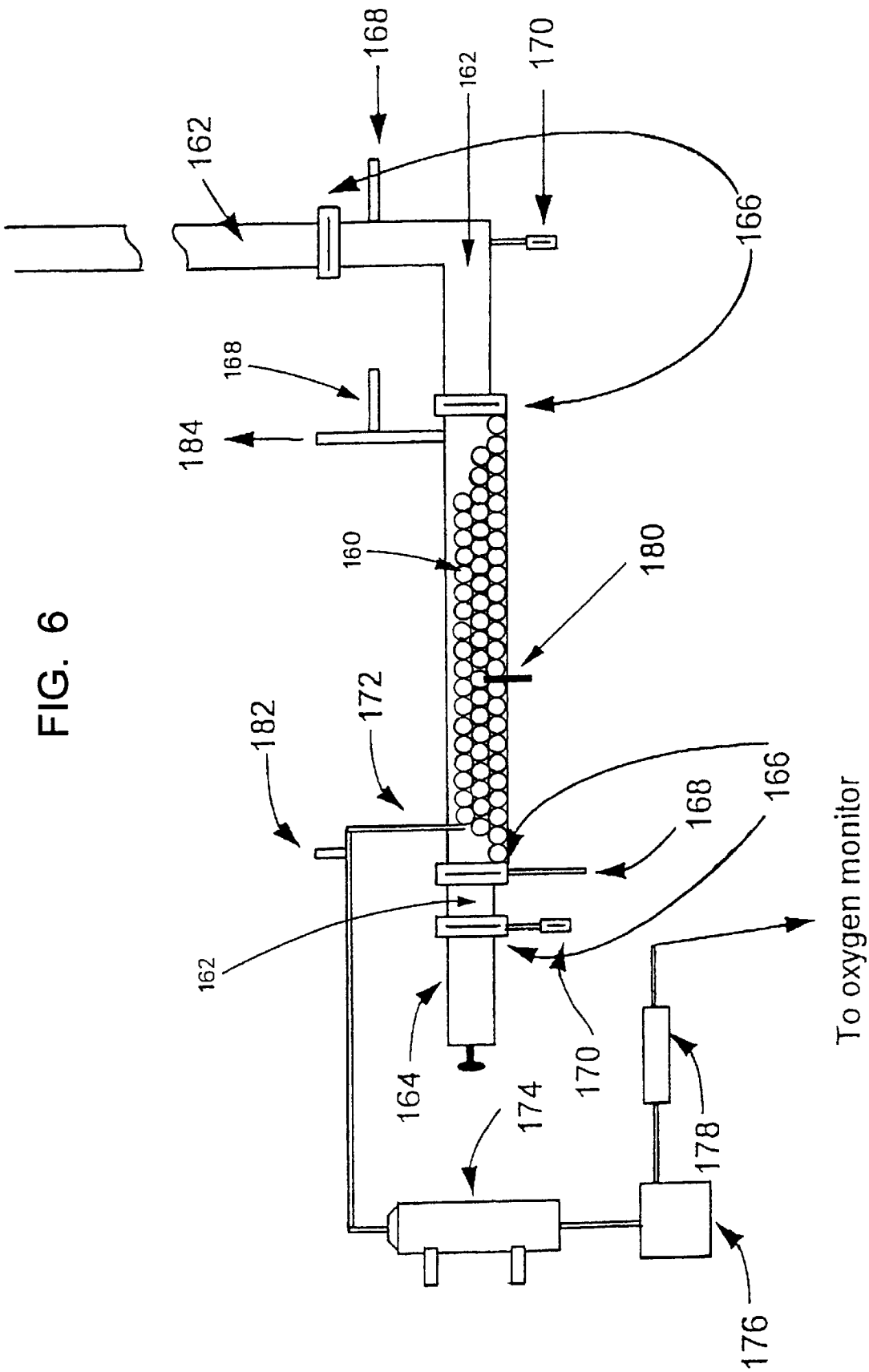
FIG. 6 is a diagrammatic view of a multi-purpose ($\pm 1000$ ml), non-resonant microwave reactor and apparatus for use in the process of the invention.

Referring to FIG. 6, there is shown a 1000 ml multi-purpose microwave apparatus fitted with a non-resonant cavity 160. The apparatus includes a 6 kW variable microwave power unit, with an operating frequency of 2.45 GHz. The unit is fitted with forward and reflected power gauges. Attached to the power unit is a waveguide 162. The waveguide 162 is fitted with a non-resonant cavity 160 and an adjustable short circuit device 164. The adjustable short circuit device 164 is used to dynamically adjust the impedance match as the load changes. To prevent diffusion of degradation products into the waveguide 162 and short circuit device 164, the cavity 160 is fitted at each end with a pair of quartz waveguide windows 166. Each quartz window 166 is sealed in specially designed flanged fittings, with a recess and special seals. Nitrogen inlets 168 purge the cavity 160 of oxygen and the section of waveguide 162 between each pair of waveguide windows 166, respectively. A methyl methacrylate Dräger tube 170 (or other suitable gas sensing device in the case of other polymers) is connected to the nitrogen outlet on the section of waveguide 162 between each pair of waveguide windows 166. Breakage of a quartz window 166 closest to the cavity 160 is indicated by a change in color of the Dräger tube 170 (caused for example in the case of PMMA, by the presence of methyl methacrylate). The gaseous product arising from the decomposition of the polymer exits the cavity through an outlet 172 (of suitable dimensions so as not to permit microwave leakage from the cavity) and passes through a condenser 174, prior to collection in a suitable collection vessel 176. A gas bomb 178 is connected to the collection vessel 176, to allow a headspace gas sample to be collected for analysis. The line between the cavity 160 and the condenser 174 is heated by heating tape, to prevent condensation of monomer in the line to the condenser 174. A thermocouple 180 is located in the lower region of the cavity 160 to monitor the temperature during depolymerization. A thermocouple 182 is located in the gas outlet pipe 172 to monitor the temperature of the gaseous products prior to condensation.

For safety, a manometer 184 is connected to the nitrogen purge inlet line 168 to monitor pressure and allow release of pressure, should a blockage occur down stream from the outlet port 172. An oxygen meter is connected to the gas exit port to monitor oxygen levels in the outlet gases. Nitrogen regulators regulate the flow of nitrogen to the various nitrogen purge lines.

The cavity is loaded with approximately 700 ml of polymer, prior to assembly to the waveguide. The system then is pureed with nitrogen and the polymer then irradiated with microwaves, once the levels of oxygen in the outlet gases are less than 0.5%. The adjustable short circuit device is adjusted during the run to minimize the reflected power. A headspace gas sample is collected (i.e from the space above the condensate) in a gas bomb, once it is evident that condensation is occurring. The run is stopped, once the temperatures measured in the cavity and gas outlet pipe begin to drop rapidly (indication that depolymerization has ceased) and no further condensate is produced (as monitored by the level of condensate in the collection vessel).

This system (FIG. 6) represents a multi-purpose microwave apparatus for testing a range of different polymers and polymer mixtures. In the examples provided (non-resonant cavity), this system was used to demonstrate the principle of depolymerization only and was not optimized for any particular polymer. Suitable adjustment of the cavity and optimization of conditions by one skilled in the art would permit maximum depolymerization of the polymer, and recovery of the monomer/monomers, for a particular polymer or polymer system.

The invention will now be further illustrated by various examples, which were carried out in the apparatus mentioned above.

All recoveries are calculated as the mass of monomer condensed as a percentage of the mass of polymer depolymerization. All yields are calculated as the mass of monomer condensed as a percentage of the total mass of polymer added to the cavity.

EXAMPLE 1
Application of the Process of the Invention to PMMA

Example 1(a)
Decomposition of poly(methyl methacrylate) in the Monomode Cavity (laboratory scale)

A sample of powdered poly(methyl methacrylate) (±1 g) was irradiated in the mono-mode microwave cavity with 200 W of forward power for 60 seconds (10% of the power was not absorbed by the material). The product condensed was analyzed for purity by a quantitative gas chromatography (GC) analysis and indicated a product purity of 99%. The polymer mass loss was 96% and the monomer yield was 86%.

Example 1(b)
Decomposition of Powdered Cast poly(methyl methacrylate) in a Mono-mode Cavity (laboratory scale)

A sample of powdered cast poly(methyl methacrylate) (<500 µm, 3.1 g) mixed with approximately 1% (m/m) carbon powder (as a microwave susceptor), was irradiated in a mono-mode microwave cavity (FIG. 1) with 1 kW of forward power for 2 minutes. The mass of the residue in the cavity, after irradiation had ceased, was determined and the polymer mass loss then calculated to be 97%. The gaseous product was analysed by Gas Chromatography—Mass Spectrometry (GCMS) and found to contain predominantly MIMA, with traces of styrene, indene, naphthalene, dimethyl terephthalate and dibutyl phthalate.

Example 1(c)
Decomposition of poly(methyl methacrylate) in a Mono Mode Cavity (bench scale reactor)

Figure 5:
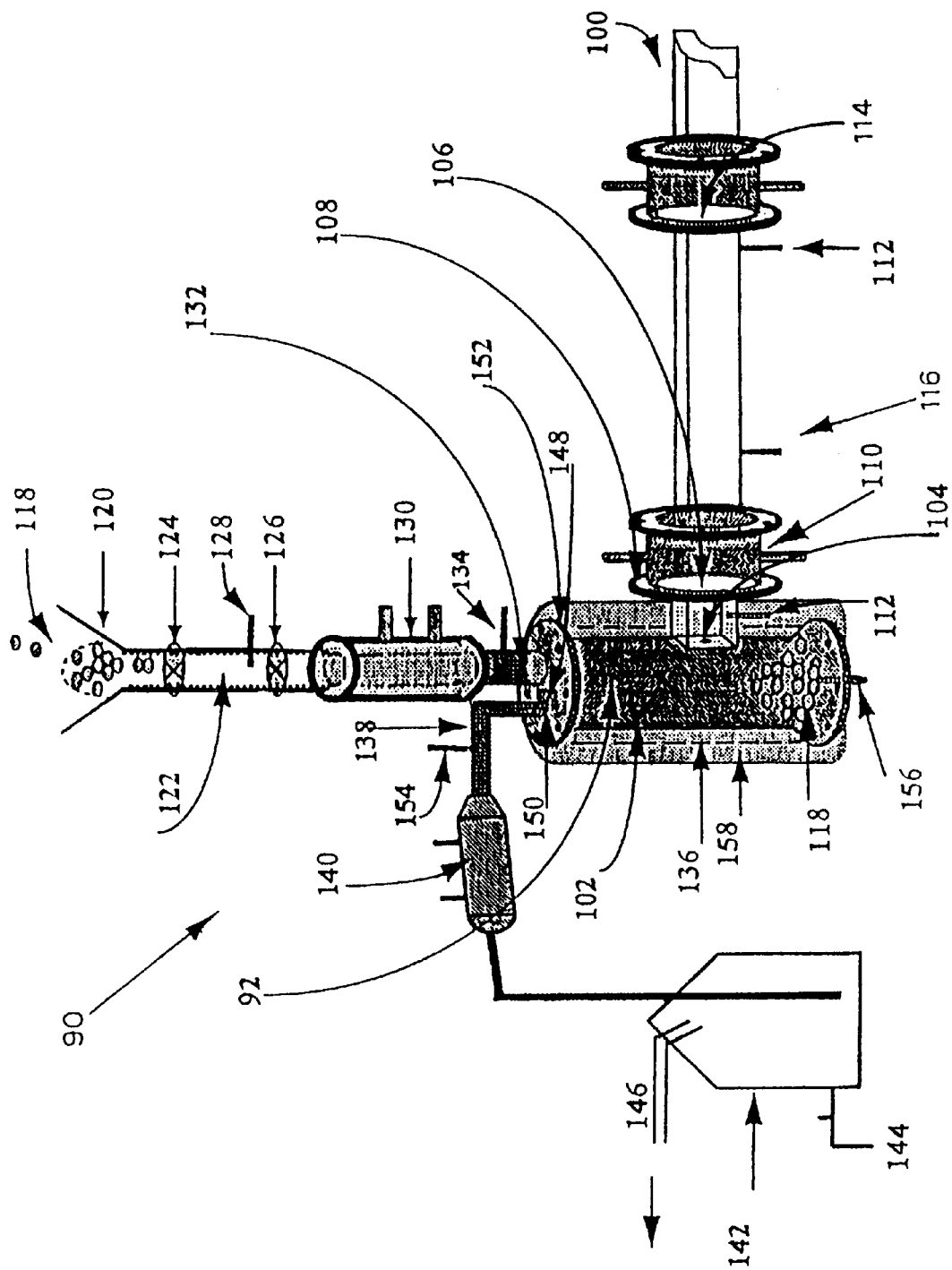
FIG. 5(a) is a diagrammatic view of a bench scale, mono-mode microwave reactor and apparatus for use in the process of the invention.
FIG. 5(b) is a diagrammatic view of a microwave variable power source for use with the reactor of FIG. 5(a)
Figure 5:
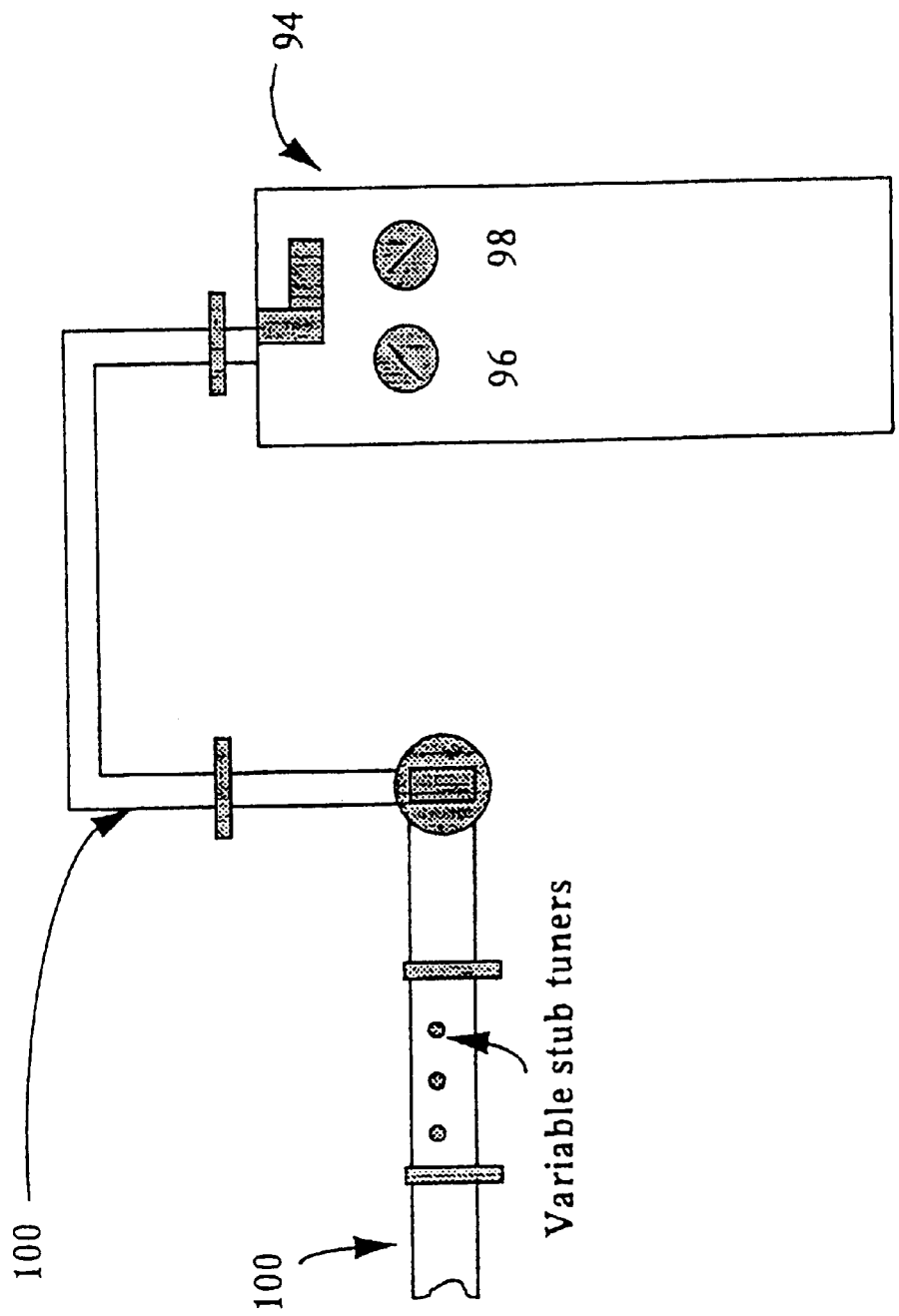

A sample of poly(methyl methacrylate) (PMMA) (220 g) was loaded into the microwave cavity (FIG. 5). The microwave reactor was heated slowly (over 2.5 hours) to a maximum of 200° C., using a heating tape wrapped around the cavity. This was done both to avoid thermal shock to the ceramic insert, and also to preheat the polymer to improve microwave coupling to the material. The forward power was then increased slowly over a 10 minute period to a maximum of 4 kW. During the experiment a further 1.647 g of PMMA was added to the reactor in small increments. whilst irradiating continuously (at 4 kW) over a period of 120 minutes. (Forward and reflected power and reaction time were not optimized during the experiment). A mass loss of 99.3% was, recorded.

An analysis of the residue in the cavity ("ash" or "dross") after irradiation was stopped, using X-ray fluorescence, showed the following composition of the "ash" or "dross", which reflects the inorganic pigments and additives in the original PMMA:

Cd(0.6%); Sr(<0.5%); Fe(0.5%); Cr(0.5%); Ti(16%); Ca(50.5%); K(<0.5%); S(4%); Al(4%); O(28%). (Other elements (Ni, Zn, Se, Cu, Si, Nd, Sb) were less than 0.1%). (Balance carbon)

(Note: During early developmental work (prior to design of the quartz window system), a high purity cylindrical alumina insert was used to line the inside of the stainless steel cavity. The narrow gap between the stainless steel wall and the ceramic insert was sealed at each end using Teflon® seals. The function of the ceramic insert (transparent to microwaves at these temperatures) was to prevent diffusion of monomer vapors into the waveguide and, thus to protect the magnetron. In view of the practical difficulties associated with this system, the improved design with a system of quartz microwave windows as described by FIG. 5 was developed and adopted in all subsequent bench scale work described herein).

Example 1(d)
Decomposition of poly(methyl methacrylate) in a Mono Mode Cavity (bench scale reactor) with Conventional Preheating During early experimental work (i.e prior to design optimization), a series of experiments was conducted where the initial temperature of the polymer (PMMA) was varied from 73° C. (run 1) to 95.3° C. (run 2), 134° C. (run 3) and finally 192° C. (run 4), and the sample irradiated under the same conditions of forward power (2 kW) for 40 minutes, with further additions of PMMA after approximately 10 minutes (50 g), 20 minutes (50 g) and 30 minutes (50 g), during each run. The following mass losses were recorded after the same total reaction time, demonstrating the beneficial effect of preheating the sample to >100° C.

| | |
|---|---|
| Run 1 (73° C.) | 46.0% |
| Run 2 (95.3° C.) | 41.9% |
| Run 3 (134.3° C.) | 80.1% |
| Run 4 (192° C.) | 81.9% |

It appears that a critical temperature exists (>100° C.), above which no further enhancement in the rate of initial mass loss is gained by increasing the temperature further. Similarly, preheating to any temperature below 95° C. gives similar initial low mass losses of around only 40–45%.

During subsequent optimization of the reactor design and other process conditions, it was found to be unnecessary to preheat PMMA. However preheating may still have a beneficial effect for other polymers.

Example 1(e)
Decomposition of poly(methyl methacrylate) in the Multi-mode Cavity (laboratory scale)

A sample of poly(methyl methacrylate) chips (±330 g) was irradiated in the multi-mode microwave cavity with 1 600 W of forward power for 23 minutes. The polymer mass loss was 98% and the product purity was 97%. (Forward and reflected power and reaction time were not optimized).

Example 1(f)
Decomposition of Clear Cast poly(methyl methacrylate) in a Mono-mode Cavity (bench scale reactor)

The walls of the microwave reactor were pre-heated to a maximum of 200° C., using a heating tape wrapped around the cavity, to prevent condensation of monomer on the walls of the cavity. The reactor system was purged with nitrogen, and the oxygen levels monitored by means of an oxygen meter placed at the exit on the collection vessel. The forward power was set at 1 kW and a sample of clear cast poly (methyl methacrylate) (130 g) was fed incrementally via the valve system into the microwave cavity over a period of about 2 minutes (FIG. 5). During the experiment, a further 5–6 kg of PMMA was added to the reactor in small increments (so as to minimize reflected power), whilst irradiating continuously (at 1 kW) over a period of 3.54 hours. The reaction temperature recorded during the depolymerization was in the range 320° C. to 390° C. An average depolymerization rate of 1.4 kg/hr was calculated. A total polymer mass loss of 98–99% was recorded. The average purity of the recovered methyl methacrylate (MMA) monomer was 95% (standard deviation 1%), and the overall MMA recovery and MMA yield, 93% (standard deviation 1%) and 90% (standard deviation 0.5%), respectively.

The actual energy utilization within the cavity was calculated as 0.714 kWhr/kg PMMA (does not take into account mains-to-magnetron electrical conversion efficiency).

An analysis of the residue in the cavity after irradiation was ceased, using Nuclear Magnetic Resonance Spectrometry (NMR), showed the presence of PMMA (only) with a molecular weight of approximately 16000.

Example 1(g)(1)
Decomposition of Pigmented or Dyed poly(methyl methacrylate) in a Mono-mode Cavity (bench scale reactor)

Using procedures identical to those conducted for Example 1(f), samples of pigmented (1 662 g) and dyed (5 053 g) PMMA were depolymerized in separate experiments over periods of 1 hour and 3 hours, respectively.

The reaction temperature recorded during the depolymerization was in the range 330° C. to 390° C. Mass losses, MMA product purities (determined by GC analysis), MMA recoveries and MMA yields were as follows:

| | Mass Loss (%) | MMA Purity (%) | MMA Recovery (%) | MMA Yield (%) |
|---|---|---|---|---|
| Pigmented PMMA | 94 | 98.1 | 94 | 88 |
| Dyed PMMA | 98 | 94.3 | 93 | 91 |

Example 1(g)(2)
Repolymerization of a Monomer to its Polymer

A sample of MMA prepared by the depolymerization of pigmented PMMA (as described in Example 1(g)(1)) was distilled at atmospheric pressure. 700 g of the distillate was activated and gently heated for 30 minutes to produce a partially polymerized, low viscosity gel (syrup). The gel was doped with various agents including a splitting aid and a peak suppressor prior to repolymerization to form a sheet of dimensions 4 mm×356 mm×356 mm. The latter PMMA sheet (produced from 100% depolymerized PMMA), was tested for ease of splitting from the casting mold, edge and sheet color, clarity, heat test quality and reduced viscosity. These results were found to be comparable to the results obtained for a typical commercially produced PMMA sheet.

Example 1(h)
Decomposition of Clear Cast poly(methyl methacrylate) in the Non-resonant Cavity A sample of clear cast poly(methyl methacrylate) chips (381 g) was irradiated in the multi-purpose, non-resonant microwave cavity (FIG. 6) with 1 kW of forward power for 20 minutes. The reaction temperature recorded during the depolymerization was in the range 360° C. to 385° C. The mass of the residue in the cavity, after irradiation had ceased, was determined and the polymer mass loss then calculated to be 58%. The MMA product purity was determined by GC analysis to be 98.7%, giving an overall MMA recovery and MMA yield of 80% and 46%, respectively.

Example 1(i)
Decomposition of Clear Extruded poly(methyl methacrylate) in the Non-resonant Cavity A sample of clear extruded poly(methyl methacrylate) chips (500 g) was irradiated in the multi-purpose, non-resonant microwave cavity (FIG. 6), with 1 kW of forward power for 36 minutes. The reaction temperature recorded during the depolymerzation was in the range 300° C. to 400° C. A headspace was sample was taken after 14 minutes of continuous microwave irradiation. The gaseous product was analysed by GCMS and found to contain: carbon dioxide; 2-methyl-1-propene; methyl acrylate and MMA. The mass of the residue in the cavity, after irradiation had ceased, was determined and the polymer mass loss calculated to be 86%. The condensate was analysed by GC and found to contain 93.4% MMA, with an overall MMA recovery and MMA yield of 60% and 52%, respectively. The condensate also was analyzed by GCMS analysis and found to contain minor impurities of: ethenyl methacrylate; methyl dimethylpentenoate; butyl methacrylate; dimethyl methylenebutanedioate; dimethyl 2-methylpentanedioate; dimethyl (methylpropenyl)propanedioate and dimethyl-1,4-cyclohexane dicarboxylate.

Example 1(j)
Decomposition of High Impact poly(methyl methacrylate) in the Non-resonant Cavity A sample of high impact poly(methyl methacrylate) chips (480 g) was irradiated in the multi-purpose, non-resonant microwave cavity (FIG. 6), with 0.5 kW of forward power for 90 minutes. The reaction temperature recorded during the depolymerization was in the range 300° C. to 415° C. A headspace gas sample was taken after 17 minutes of continuous microwave irradiation. The gaseous product was analyzed by GCMS and found to contain: carbon dioxide; 2-methyl-1-propene; ethyl acrylate; MMA and methyl-2-methylpropanoate. The mass of the residue in the cavity, after irradiation had ceased, was determined and the polymer mass loss then calculated to be 85%. The condensate was analyzed by GC and found to contain 71.7% MMA, with an overall MMA recovery and MMA yield of 47% and 40%, respectively. The condensate also was analyzed by GCMS and found to contain minor quantities of: ethyl methacrylate; styrene; butyl acrylate; methyl dimethylpentenoate and butyl methacrylate.

Example 1(k)
Decomposition of poly(methyl) methacrylate) Swarf in a Mono-mode Cavity (laboratory scale)

A sample of poly(methyl methacrylate) swarf ("sawdust") (2.1 g) mixed with approximately 1% (m/m) carbon powder (as a microwave susceptor), was irradiated in a mono-mode microwave cavity (FIG. 1), with 1 kW of forward power for 2 minutes. The mass of the residue in the cavity, after irradiation had ceased, was determined and the polymer mass loss then calculated to be 98%. The gaseous product was analyzed by GCMS and found to contain predominantly MIMA, with traces of styrene, naphthalene and dibutyl phthalate.

Example 1(l)
Decomposition of poly(methyl methacrylate) Gel in a Mono-mode Cavity (laboratory scale)

A sample of poly(methyl methacrylate) gel (partially polymerized MMA from the plant) (0.8 g), mixed with approximately 1% (m/m) carbon powder (as a microwave susceptor), was irradiated in a mono-mode microwave cavity (FIG. 1), with 1 kW of forward power for 2.5 minutes. The mass of the residue in the cavity, after irradiation had ceased, was determined and the polymer mass loss then calculated to be 84% The gaseous product was analyzed by GCMS and found to contain predominantly MMA, with traces of xylene, styrene, 2-methyl propanenitrile and methyl 2-methylbutanoate.

Example 2
Application of the Process of the Invention to Physical Mixtures of Polymers

Example 2(a)(1)
Decomposition of a Physical Mixture of Polymers, where Both Polymeric Substances Decompose to their Corresponding Monomers A sample of clear cast poly(methyl methacrylate) chips (231 g) and clear polystyrene pellets (231 g), was irradiated in a multi-purpose, non-resonant microwave cavity (FIG. 6), with 1 kW of forward power for 60 minutes. The reaction temperature recorded during the depolymerization was in the range 330° C. to 400° C. A headspace gas sample was taken after 22 minutes or continuous microwave irradiation. The gaseous product was analyzed by GCMS and found to contain: MMA; 2-methyl-1-propene; carbon dioxide, and traces of methyl 2-methylpropanoate; toluene and styrene. The mass of the residue in the cavity, after irradiation had ceased, was determined and the total polymer mass loss calculated to be 70%. The condensate was analyzed by NMR and found to contain 29% (m/m) MMA and 64% (m/m) styrene, giving a yield of MMA and styrene of 31% and 67%, respectively. The condensate also was analyzed by GCMS and found to contain minor quantities of methyl styrene, styrene dimer and trimer, as well as traces of toluene.

Example 2(a)(2)
Separation of Two Monomers Recovered in Liquid Form, by Distillation The condensate produced as described in Example 2(a) (1), and containing 29% (m/m) MMIA and 64% (m/m) styrene, was distilled under a vacuum of 60–70 kPa. During the distillation, the temperature was increased incrementally from 25 to 150° C., over approximately 6 hours. The first fraction collected was analyzed by NMR and found to contain 84% (m/m) MMA and 6% (m/m) styrene. The final fraction, also analyzed by NMR, was found to contain 72% (m/m) styrene and 18% (m/m) MMA. Optimization of the distillation procedure, would improve the separation of the monomers.

Example 2(b)
Decomposition of a Physical Mixture of Polymers, where Both Polymeric Substances Decompose, but Only One, to its Corresponding Monomer A mixture of clear cast poly(methyl methacrylate) chips (209 g) and clear polyethylene beads (209 g) was irradiated in a multi-purpose, non-resonant microwave cavity (FIG. 6), with 1 kW of forward power for 45 minutes. The reaction temperature recorded during the depolymerization was in the range 300° C. to 390° C. A headspace gas sample was taken after 25 minutes of continuous microwave irradiation. The gaseous product was analyzed by GCMS and found to contain predominantly MMA, 2-methyl-1-propene and carbon dioxide. The mass of the residue in the cavity, after irradiation had ceased, was determined and the total polymer mass loss calculated to be 38%. The condensate was analyzed by GC and found to contain 97.6% MMA. The condensate also was analyzed by GCMS and found to contain minor quantities of 2-methylbutanoate ester, esters of pentane and hexane, styrene, styrene dimer and $C_{14}H_{28}$, and $C_{16}H_{32}$.

Example 2(c)
Selective Decomposition of a Physical Mixture of Polymers, where the Decomposition Temperature and the Dielectric Loss Factors are Significantly Different A sample of clear cast poly(methyl methacrylate) chips (243 g) and polytetrafluoroethylene powder (243 g), was irradiated in a multi-purpose, non-resonant microwave cavity (FIG. 6), with 1 kW of forward power for 40 minutes. The reaction temperature recorded during the depolymerization was in the range 300° C. to 390° C. A headspace gas sample was taken after 15 minutes of continuous microwave irradiation. The gaseous product was analyzed by GCMS and found to contain MMA, 2-methyl-1-propene and carbon dioxide. The mass of the residue in the cavity, after irradiation had ceased, was determined and the total polymer mass loss then calculated to be 36%. The condensate was analyzed by GC and found to contain 99.6% MMA.

Example 3
Application of the Process of the Invention to polystyrene (PS)

Example 3(a)
Decomposition of polystyrene in the Mono-mode Cavity (laboratory scale)

A sample of polystyrene (±0.5 g) and carbon (20% by mass) were irradiated in the mono-mode microwave cavity (FIG. 1) with 1 kW of forward power for 60 seconds. Styrene monomer was recovered from the gases evolved. (Forward and reflected power and reaction time were not optimized).

Example 3(b)
Decomposition of polystyrene in a Non-resonant Cavity

A sample of clear polystyrene pellets (481 g) and 10% (m/m) carbon pellets, was irradiated in a multi-purpose, non-resonant microwave cavity (FIG. 6), with 0.5 kW of forward power for 15 minutes followed by 1 kW of forward power for 10 minutes. The reaction temperature recorded during the depolymerization was in the range 200° C. to 290° C. A headspace gas sample was taken after 24 minutes of continuous microwave irradiation. The gaseous product was analyzed by GCMS and found to contain styrene, carbon dioxide, benzene, ethylbenzene and toluene. The mass of the residue in the cavity, after irradiation had ceased, was determined and the polymer mass loss then calculated to be 21%. The condensate was analyzed by NMR and found to contain approximately 60% (m/m) styrene, 30% (m/m) styrene trimer and styrene dimer, 6% (m/m) ethylbenzene and 4% (m/m) toluene. The condensate also was analyzed by GCMS and found to contain small quantities of (1-methylethyl) benzene; (1-methylethenyl) benzene; and benzene. The latter compounds were not detected by NMR, as the signals for these compounds were masked by the signals of other compounds, present in larger quantities.

Example 4
Application of the Process of the Invention to poly(ethylene terephthalate) (PET)

Example 4(a)
Decomposition of poly(ethylene terephthalate) in the Mono-mode Cavity A sample of poly(ethylene terephthalate) (2.01 g)mixed with (0.09 g) carbon (as a microwave susceptor, 4.36% m/m) was irradiated in a mono-mode cavity using a forward power of 1 kW and a total irradiation time of 5 minutes (neither power nor reaction time was optimized). A mass loss of 66.7% was recorded. The gaseous product was analyzed and found to contain carbon dioxide, acetaldehyde and benzene as the major products. The residue, was found to contain predominantly terephthalic acid, one of the valuable monomers used in the manufacture of PET, with a small amount of unreacted PET.

Example 4(b)
Decomposition of poly(ethylene terephthalate) in a Non-resonant Cavity A sample of clear poly(ethylene terephthalate) (PET) pellets (717 g) and 10% (m/m) carbon pellets, was irradiated in a multi-purpose, non-resonant microwave cavity (FIG. 6) with 0.5 kW of forward power for 30 minutes. The reaction temperature recorded during the depolymerization was in the range 400° C. to 470° C. A headspace gas sample was taken after 12 minutes of continuous microwave irradiation. The gaseous product was analyzed by GCMS and found to contain predominantly carbon dioxide and acetaldehyde. Minor quantities of benzene, ethylbenzene, toluene and styrene were also found to be present in the gas sample. As expected, no condensate was formed during this run. The solid product deposited on the walls of the cavity (outside the reaction zone), was analyzed by NMR and found to contain approximately 44% (m/m) terephthalic acid and 56% (m/m) hydroxy (vinyloxycarbonyl) benzoic acid.

Example 5
An Illustration of Polymers which Do Not Degrade to Monomers

Example 5(a)
Decomposition of polyethylene in a Mono-mode Cavity (laboratory scale)

A sample of polyethylene (2.4 g) mixed with approximately 14% (m/m) carbon powder (as a microwave susceptor), was irradiated in a mono-mode microwave cavity (FIG. 1), with 2 kW of forward power for 2 minutes. The gaseous product was analyzed by GCMS and found to contain propene. hexene, benzene, heptene, as major products and octene, nonene, styrene, 1-propyl benzene, and hydrocarbons with 10 to 23 carbons, as minor products.

Example 5(b)
Decomposition of polypropylene in a Mono-mode Cavity (laboratory scale)

A sample of polypropylene (1.5 g) mixed with approximately 15% (m/m) carbon powder (as a microwave susceptor), was irradiated in a mono-mode microwave cavity (FIG. 1), with 1 kW of forward power for 30 seconds. The gaseous product was analyzed by GCMS and found to contain propene, hexene, benzene and nonene, as major products, toluene and styrene as minor products, and traces of 1 propynyl benzene, 2 dodecene, naphthalene, $C_{15}H_{30}$, $C_{16}H_{32}$, $C_{12}H_{10}$, $C_{14}H_{10}$ and $C_{16}H_{10}$.

The process of the invention has various advantages over the known conventional process for the decomposition of polymers. The advantages of the process of the invention include increased product purity, potentially eliminating the need for ocher downstream processing steps, minimal environmental impact, greater energy efficiency due to direct volumetric heating of the polymer, improved occupational health and safety features, and reduced solid waste accumulation. The improved energy efficiency and reduced effluent volumes (such as wash effluent and lead dross in the case of PMMA) provide significant operational cost advantages to the microwave process over alternative and more conventional depolymerization processes, despite an initially higher capital investment.

In particular the invention provides a process, which is of particular use with poly(methyl methacrylate) as the polymeric species. Based on extensive bench scale (1.5 kg/hr) studies on PMMA, a comparison of the costs of production (variable, excluding cost of scrap PMMA, and fixed operating costs, excluding depreciation) for the microwave and lead bath processes shows savings of 74% in the microwave process over the lead bath. This is due to the fact that energy costs can be reduced by up to 61%, while costs of chemicals can be reduced by 87%, by eliminating downstream processing steps (e.g washing). Furthermore, elimination of solid and aqueous effluents considerably reduces the costs of effluent disposal and environmental monitoring by up to 94%. Including the cost of scrap PMMA, this translates to savings of 11% on the cost of production for the microwave process, over the lead bath.

What is claimed is:

1. A process for decomposing a polymer which is capable of undergoing thermal depolymerization to its monomer or monomers, the polymer being selected from the group consisting of poly(methyl methacrylate), polytetrafluoroethylene, polystyrene, poly(ethylene terephthalate), poly($\alpha$-methylstyrene) and polyisobutylene, and for recovery of at least one of the monomers, includes the steps of:

(i) subjecting the polymer in solid, eel, partially molten or molten form to microwave heating for a time and at a temperature sufficient to decompose the polymer to produce the monomer or monomers in gaseous, liquid or solid form, without substantial decomposition of the monomer or monomers; and (ii) recovering at least one of the monomer or monomers.

2. A process according to claim 1 wherein the process includes the step of:

(iii) where two or more monomers are recovered in step (ii), separating the monomers from one another.

3. A process according to claim 1 wherein the process includes the step of:

(iv) where the monomer or monomers are in gaseous form, condensing the monomer or monomers.

4. A process according to claim 1 wherein the process includes the step of:

(v) purifying the condensed monomer or monomers.

5. A process according to claim 1 wherein prior to step (i) the polymer is preheated to a suitable temperature.

6. A process according to claim 1 wherein in step (i) the polymer is mixed with a microwave absorber or susceptor.

7. A method according to claim 1 wherein step (i) is carried out under an inert atmosphere.

8. A process according to claim 1 wherein in step (i) the microwave heating is carried out in a mono-mode, a multi-mode, or a non-resonant cavity of a microwave reactor.

9. A process according to claim 1 wherein the polymer is selected from the group consisting of poly(methyl methacrylate), polytetrafluoroethylene, poly( -methylstyrene), polystyrene and, polyisobutylene.

10. A process according to claim 9 wherein the polymer is poly(methyl methacrylate).

11. The use of a monomer produced by a process according to claim 1, in a process for the polymerization of the monomer, optionally with one or more additional monomers, and optionally mixed with virgin monomer, to produce a polymer.

12. A process for the production of a polymer from a monomer produced by the process of claim 1 wherein the monomer is polymerized, optionally with one or more additional monomers, and optionally mixed with virgin monomer.

* * * * *